(12) United States Patent
Kawasaki et al.

(10) Patent No.: US 7,790,938 B2
(45) Date of Patent: Sep. 7, 2010

(54) PROCESS FOR PRODUCING ALCOHOL

(75) Inventors: Hiroki Kawasaki, Okayama (JP); Yuichi Fujita, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/144,621

(22) Filed: Jun. 6, 2005

(65) Prior Publication Data

US 2005/0277793 A1   Dec. 15, 2005

Related U.S. Application Data

(63) Continuation of application No. PCT/JP03/14841, filed on Nov. 20, 2003.

(30) Foreign Application Priority Data

Dec. 4, 2002   (JP) .................... P. 2002-352760

(51) Int. Cl.
*C07C 29/14* (2006.01)
(52) U.S. Cl. .................................... 568/880
(58) Field of Classification Search ............... 568/880
See application file for complete search history.

(56) References Cited

U.S. PATENT DOCUMENTS

| 2,571,160 | A | * | 10/1951 | Hillard, Jr. et al. ......... 568/882 |
| 4,138,588 | A | | 2/1979 | Tummes et al. |
| 4,518,809 | A | * | 5/1985 | Forster et al. ............... 568/840 |
| 6,455,743 | B1 | * | 9/2002 | Ueda et al. .................. 568/881 |

FOREIGN PATENT DOCUMENTS

| CN | 1221723 | | 7/1999 |
| CN | 1349484 | | 5/2002 |
| JP | 2-164837 | | 6/1990 |
| JP | 6-122638 | | 5/1994 |
| JP | 06122638 A | * | 5/1994 |
| JP | 06-122638 | * | 6/1994 |
| JP | A-7-278032 | | 10/1995 |

OTHER PUBLICATIONS

U.S. Appl. No. 11/144,590, filed Jun. 6, 2005, Kawasaki, et al.

* cited by examiner

*Primary Examiner*—Peter G O'Sullivan
*Assistant Examiner*—Sudhakar Katakam
(74) *Attorney, Agent, or Firm*—Oblon, Spivak, McClelland, Maier & Neustadt, L.L.P.

(57) ABSTRACT

The invention relates to a process for producing an alcohol including hydrogenating an aldehyde using a hydrogenation catalyst and subjecting the resultant product to distillation/purification, wherein the resultant hydrogenation product is subjected to distillation/purification in the absence of the hydrogenation catalyst or in the presence of the hydrogenation catalyst in such an amount that does not cause a dehydrogenation reaction.

19 Claims, 1 Drawing Sheet

PROCESS FOR PRODUCING ALCOHOL

TECHNICAL FIELD

The present invention relates to a process for producing an alcohol. More specifically, it relates to a process for producing an alcohol comprising hydrogenating an aldehyde and purifying the product, wherein an aldehyde concentration contained in the product alcohol is remarkably reduced than before.

BACKGROUND ART

As a process for producing an alcohol, a method of obtaining the alcohol by hydrogenating an aldehyde and purifying the product is hitherto known and has been commercialized worldwide. For example, with regard to saturated aldehydes, butyraldehyde can be hydrogenated to afford butanol and nonyl aldehyde can be hydrogenated to afford nonanol, and with regard to unsaturated aldehyde, 2-ethylhexenal can be hydrogenated to afford 2-ethylhexanol, 2-propylheptenal can be hydrogenated to afford 2-propylheptanol, and decenal can be hydrogenated to afford decanol.

As the mode of the hydrogenation reaction, it is common to use a reactor, inside of which is usually packed with a nickel-based or cooper-based solid hydrogenation catalyst. There are a mode where a starting aldehyde is vaporized to carrying out the reaction in a vapor phase and a mode where a starting aldehyde is introduced as a liquid into a reactor to carrying out in a liquid phase.

However, regardless of the catalyst species and the reaction mode of vapor phase/liquid phase, there are problems that esterification, acetalization, etherification, and the like occur as undesirable side reactions to lower the selectivity of the reaction in any of the conventional reaction processes and also a satisfactory product alcohol cannot be obtained unless these by-products are separated/removed by distillation operation or the like for purification in a subsequent step.

As the purification/distillation method of the above crude alcohol, the following methods have been proposed, for example.

The first method is a method of separating low-boiling products in a first column, then separating the alcohol from high-boiling products by distillation to obtain the alcohol product as a distillate from the column top by operating column top pressure in the second column, and recovering useful products in high-boiling components by operating the column top pressure in the third column (3-column mode).

Specifically, in Patent Document 1 (JP-B-49-11365), there is described a method wherein purified 2-ethylhexanol is obtained by operating the second column under the conditions of a column top pressure of 200 to 800 mmHg and a column bottom alcohol content of 50 wt % or more and by operating the third column under the condition of a column top pressure of 70 to 300 mmHg in the above 3-column mode.

Moreover, there is also known a method wherein the first column is carried out in two steps in the above 3-column mode (4-column mode), i.e., a method wherein low-boiling products are separated as a distillate in the first column; then the product alcohol was distilled in the second column; the bottom liquid was further concentrated in the third column and, after high-boiling products were separated from the bottom, effective components are recovered by distillation; and the low-boiling products separated in the first column was further concentrated and separated by distillation in the fourth column and effective components are recovered from the bottom.

Additionally, in order to avoid contamination of the alcohol product distilled from the column top with low-boiling products formed by thermal decomposition of the high-boiling components in the bottom liquid, particularly acetal components, ether components, and the like in the above second column from which the product alcohol is obtained, there is also known a method wherein high-boiling components are separated in the first column, a fraction containing low-boiling components and the alcohol and containing substantially no high-boiling components is distilled from the column top, the fraction is fed to the second column and the low-boiling components are separated from the alcohol, and a fraction containing the low-boiling components as main components is distilled from the column top while purified alcohol is distilled as a side cut (cf. Patent Document 2).

Furthermore, in the above 2-column mode, there is disclosed a method wherein the high-boiling components are positively thermally cracked by maintaining the bottom temperature to the value calculated from a prescribed equation or higher and the concentration of the high-boiling components in the bottom liquid to 30 wt % or more in the first column from which the high-boiling components are separated and the high-boiling components are recovered as effective components (cf. Patent Document 3).

On the other hand, in general, since the product alcohol is frequently used mainly as a plasticizer for resins such as vinyl chloride, an extremely high purity is required and a little coloring, i.e., a little degree of coloring in the sulfuric acid coloring test, which is conducted by heating a sample together with sulfuric acid and then measuring the degree of coloring, is required.

As a component extremely strongly affecting the above sulfuric acid coloring test or the like, an aldehyde may be mentioned. This is because an aldehyde is an unsaturated hydrocarbon. Therefore, the aldehyde concentration of the product alcohol is one of the most important items for quality of the product alcohol and is desirably reduced.

However, relatively a large amount of the aldehyde is contained in the product alcohol obtained by any method in the above prior art and thus the product is not thoroughly satisfactory. However, in the above prior art, the concentration of the aldehyde contained in the product alcohol is not at all focused and hence no method for lowering the concentration is disclosed. This may be attributed to the fact that the following can be easily supposed for one skilled in the art when considered based on common knowledge of chemical engineering without particular disclosed technology.

That is, as methods for reducing the concentration of the aldehyde contained in the product alcohol, there may be considered 1) a method of reducing the amount of unreacted aldehyde to be introduced into the purification system by increasing the conversion rate of the aldehyde into the alcohol in the hydrogenation reaction; 2) a method of increasing the degree of separation of the aldehyde as a low-boiling component by increase of the plate number of the distillation column, increase of reflux ratio, or the like in the step of separating low-boiling components in the purification system; and the like method.

In the actual commercial running, it is supposed that the maintenance of the quality of the product alcohol, i.e., the concentration of the aldehyde contained to a standard value or lower may be achieved by the following methods: reduction of the amount of unreacted aldehyde to be introduced into the purification system by changing running conditions such as reaction temperature and the like to suppress the decrease of conversion rate of the aldehyde, the decrease being induced with the decrease of activity of the hydrogenation catalyst with the passage of time (i.e., the method of the above 1)) or increase of the separation efficiency of the aldehyde by increasing the reflux amount or the distillate amount in the low-boiling component-separating column in the purification system (i.e., the method of the above 2)).

However, currently it is very difficult to obtain an alcohol having a low concentration of an aldehyde.

On the other hand, in the purification/distillation of $C_3$-$C_{10}$ alcohols, it is confirmed that corresponding aldehydes are formed by heat load at the bottom part of the distillation column and a method of distillation in the presence of an alkali metal hydroxide is disclosed as a suppressing means (cf. Patent Document 4).

However, in the method, there is a problem that an additional facility for adding the alkali metal hydroxide is necessary and it is impossible to deny the possibility of contamination of the additive into the product alcohol

[Patent Document 1] JP-B-49-11365
[Patent Document 2] JP-A-6-122638
[Patent Document 3] JP-A-7-278032
[Patent Document 4] JP-T-11-500437

DISCLOSURE OF THE INVENTION

In order to reduce the concentration of the aldehyde contained, the present inventors have attempted various ways of operational adjustment in commercial running for many years using the aforementioned chemical engineering techniques. However, even when the conversion is increased in the hydrogenation or even when the separation rate of the low-boiling components in the low-boiling component-separation column which is a distillation column for separating the aldehyde from the product alcohol in the purification system, they have experienced hardship that the aldehyde concentration in the product alcohol cannot be reduced to less than a specific value.

The product quality should be maintained as a matter of first priority and hence the aldehyde concentration in the product alcohol should be maintained at a predetermined low level. As operational adjustment for the purpose, change of reaction conditions such as change of the reaction temperature to a higher temperature side is necessary for the purpose of increasing the conversion rate of the aldehyde in the hydrogenation reaction. As a result, since the by-product formation rate of the high-boiling components increases even when the conversion rate of the aldehyde is increased, decrease in an alcohol yield and increase in purification/separation costs for the high-boiling components are unavoidable.

Moreover, the countermeasure in the purification system, i.e., the increase of the degree of separation of the low-boiling components by distillation corresponds to the increase in the reflux amount and the distillate amount or the increase in the theoretical plate number of the distillation column, which means increase of running costs for reboiler heat source and facility costs. They result in large increase of burden, which is economically not at all negligible.

Furthermore, even when the aldehyde formation due to heat load is suppressed by lowering the temperature of the bottom of the distillation column to 150° C. or lower through distillation under a pressure lower than atmospheric pressure, the aldehyde concentration in the product alcohol cannot be reduced to less than a specific value.

Namely, the invention solves the above problems and an object thereof is to obtain a highly pure alcohol by reducing the aldehyde concentration in the product alcohol efficiently and inexpensively.

As a result of the collection and analysis of plant data in actual commercial operations and the precise studies on material balance in the plant for the purpose of the investigation of fundamental measures against the above problems, the inventors have found a surprising fact. That is, they have found that total amount of the aldehyde discharged from the purification system to the outside of the system, i.e., total amount thereof in all efflux streams such as the aldehyde in the product and the aldehyde in a separated low-boiling component stream is always much larger than the amount of the unreacted aldehyde contained in the hydrogenation product introduced into the purification system from the hydrogenation reaction system, although the bottom temperature of the distillation column is low and hence heat load is a little.

This fact indicates that the aldehyde is formed in the purification system by some cause other than heat load. As a result of more precise investigation on the place where it is formed, they have found that, in a system wherein a low-boiling component-separating column is employed as the first column and a product column is employed as the second column, for example, an amount of the aldehyde several times larger than the amount of remaining aldehyde not separated in the first column and introduced from the first column to the second column is contained in the distilled product alcohol of the second column which is the product column, although most of the aldehyde is separated/removed from the column top in the first column which is the low-boiling component-separating column.

Namely, they have found that the aldehyde is formed even in the inside of the product column to which a little heat load is applied.

As a result of investigations on the causes of the aldehyde formation in the purification system of the commercial plant from various angles, they have found that a pulverized powder of the hydrogenation catalyst is present although the amount is very little, when the column bottom liquid in the purification system and the hydrogenation product liquid fed from the hydrogenation reactor to the purification system are analyzed. Thus, they have obtained a finding as a method for forming substantially no aldehyde in the purification system by removing most of the powder of the hydrogenation catalyst and have accomplished the invention.

Namely, the gist of the invention lies in the following (1) to (7).

(1) A process for producing an alcohol comprising hydrogenating an aldehyde using a hydrogenation catalyst and subjecting the resultant product to distillation/purification, wherein the resultant hydrogenation product is subjected to distillation/purification in the absence of the hydrogenation catalyst or in the presence of the hydrogenation catalyst in such an amount that does not cause a dehydrogenation reaction.

(2) A process for producing an alcohol comprising hydrogenating an aldehyde using a hydrogenation catalyst and subjecting the resultant product to distillation/purification, wherein a step of removing the hydrogenation catalyst from the hydrogenation product is provided between the hydrogenation step and the distillation/purification step.

(3) The process for producing an alcohol according to the above (1) or (2), wherein the hydrogenation reaction is carried out in a liquid phase.

(4) The production process according to the above (2) or (3), wherein the removal of the hydrogenation catalyst is achieved by means of a filter.

(5) The production process according to any one of the above (1) to (4), wherein the aldehyde is an aldehyde having 3 to 10 carbon atoms formed by hydroformylation or a dimerized aldehyde obtained by a further aldol condensation/dehydration reaction of the aldehyde having 3 to 10 carbon atoms formed by hydroformylation.

(6) The production process according to any one of the above (1) to (5), wherein a conversion rate of the aldehyde is 98% or more in the hydrogenation step and concentration of the aldehyde contained in the product alcohol is 0.05 wt % or less.

(7) The production process according to any one of the above (1) to (6), wherein concentration of the hydrogenation catalyst in the hydrogenation product to be fed to the distillation/purification step is 100 ppm or less.

Figure 1:
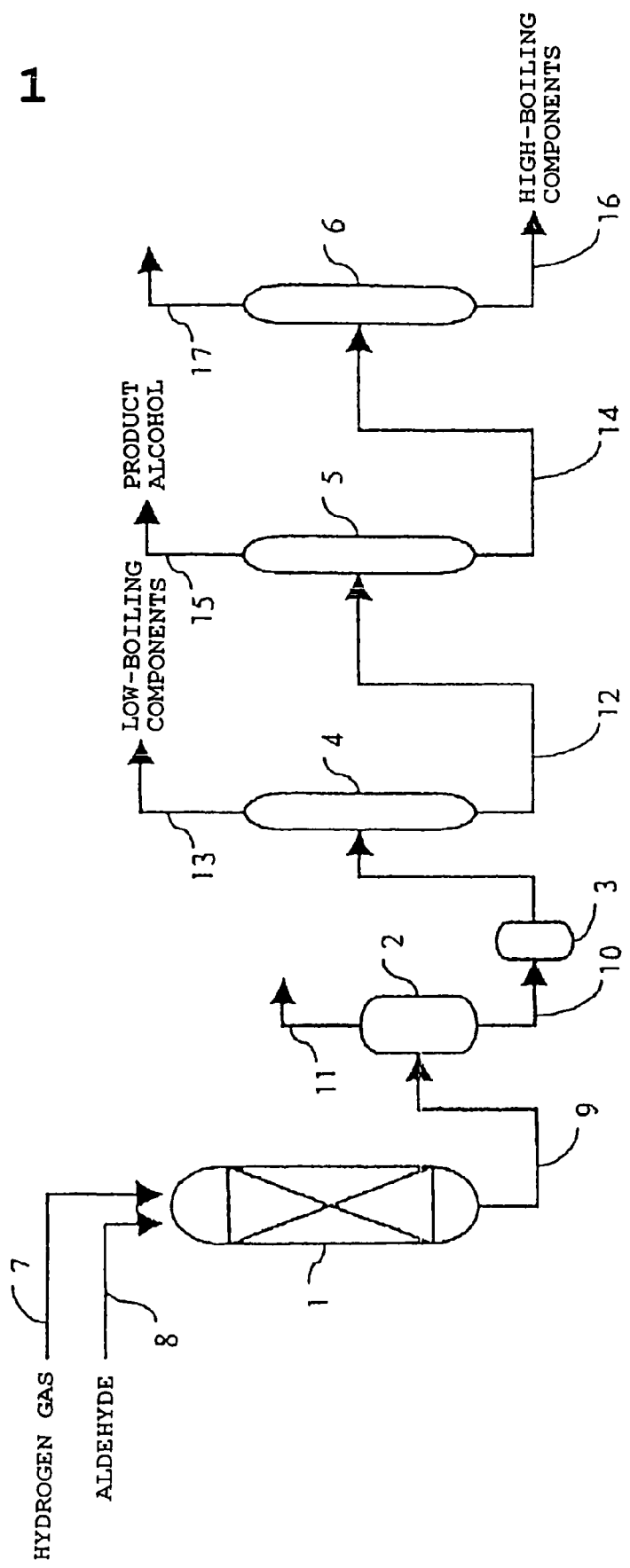
FIG. 1 is a schematic diagram of an alcohol production process.

Incidentally, reference numerals and signs in the drawing are as follows. 1 represents a hydrogenation reactor, 2 represents a gas-liquid separator, 3 represents a catalyst powder-removing apparatus, 4 represents a low-boiling component-separating distillation column, 5 represents a product-purifying distillation column, and 6 represents a high-boiling component-separating distillation column.

BEST MODE FOR CARRYING OUT THE INVENTION

The following will explain the present invention in further detail.

The aldehyde, which is a starting material for the alcohol, to be used in the invention is not particularly limited and there may be used a saturated aldehyde having at least 3 carbon atoms, usually 3 to 10 carbon atoms, a dimerized unsaturated aldehyde obtained by further aldol condensation/dehydration reaction thereof, a mixture thereof, or the like.

The saturated aldehyde includes linear and branched aldehydes. Specifically, there may be mentioned propionaldehyde, butyraldehyde, heptyl aldehyde, nonyl aldehyde, undecyl aldehyde, tridecyl aldehyde, hexadecyl aldehyde, heptadecyl aldehyde, and the like.

Moreover, as the unsaturated aldehyde, there may be mentioned 2-ethylhexenal, 2-propylheptenal, decenal, and the like.

Of these, preferred are butyraldehyde, nonyl aldehyde, 2-ethylhexenal, and 2-propylheptenal.

In the invention, the process for producing the aforementioned aldehydes is not limited. For example, in the case of the saturated aldehyde, there may be mentioned a process for forming an aldehyde by widely commercialized hydroformylation of an olefin, more precisely by hydroformylation of an olefin with oxo gas in the presence of a Group VIII metal complex catalyst having an organophosphorus compound as a ligand, or the like.

Moreover, in the case of the unsaturated aldehyde, it is obtained by an aldol condensation/dehydration reaction of a saturated aldehyde. As the aldol condensation/dehydration reaction, there may be mentioned a method of obtaining an unsaturated aldehyde by dimerizing an aldehyde, which is formed by the above hydroformylation or the like, using an aqueous solution of an alkali such as sodium hydroxide as a catalyst.

In the invention, a commercially available aldehyde can be, of course, employed as the aldehyde.

In the process of the invention, the aforementioned aldehyde is first hydrogenated using a hydrogenation catalyst (hereinafter, sometimes referred to as hydrogenation step).

As the hydrogenation catalyst, any one hitherto known can be employed. For example, there may be mentioned solid hydrogenation catalysts wherein an active component such as nickel, chromium, or copper is supported on a support such as diatomaceous earth or celite. In particular, preferred in the invention is a catalyst wherein nickel and/or chromium are supported as active component(s) on diatomaceous earth as a support. In the hydrogenation reaction of the above aldehyde, the corresponding alcohol is formed by carrying out the reaction usually under the reaction conditions of atmospheric pressure to 150 atm and 40 to 200° C. using the above hydrogenation catalyst.

The reaction may be carried out in a vapor phase by vaporizing a starting aldehyde or may be carried out in a liquid phase by introducing the starting aldehyde as a liquid into a reactor. In the invention, the reaction is preferably carried out in a liquid phase.

In the invention, the conversion rate of the aldehyde in the hydrogenation step is not limited but is desirably in the range of 80 to 99.99%, more preferably 98% or more since the amount of the aldehyde contained in the product alcohol may increase when the conversion rate is too low.

In the invention, in the process on the premise of such a high conversion rate of the aldehyde, it is possible to produce a highly pure alcohol stably without unduly increasing the scale and load of the purification facility.

In the invention, it is essential to subject the resultant hydrogenation product in the absence of the hydrogenation catalyst or in the presence of the hydrogenation catalyst in such an amount that does not cause a dehydrogenation reaction to distillation/purification. As one embodiment therefor, it may be mentioned to provide a step of removing the hydrogenation catalyst from the hydrogenation product between the hydrogenation step and the distillation/purification step.

In this connection, "in the presence of the hydrogenation catalyst in such an amount that does not cause a dehydrogenation reaction" refers to "in the presence of the hydrogenation catalyst in such an amount that can suppress a dehydrogenation reaction so that the aldehyde concentration contained in the product alcohol does not degrade the quality of the product, preferably so that the aldehyde concentration contained in the product alcohol does not reach 0.05 wt % or more". Specifically, the concentration of the hydrogenation catalyst in the hydrogenation product is preferably 500 ppm or less, more preferably 100 ppm or less, particularly preferably 50 ppm or less. When the concentration of the hydrogenation catalyst is too high, the aldehyde is formed in the distillation/purification step.

The following will explain the step of removing the hydrogenation catalyst from the hydrogenation product (hereinafter, sometimes referred to as catalyst-removing step), prior to the purification step by distillation or the like.

The method for removing the solid hydrogenation catalyst is not limited and can be achieved by means of a filter, a centrifuge, a simple distillation apparatus, or the like. Particularly, the removal is preferably achieved by means of a filter.

The concentration of the hydrogenation catalyst in the hydrogenation product after the catalyst-removing step is preferably 500 ppm or less, more preferably 100 ppm or less, particularly preferably 50 ppm or less. When the concentration of the hydrogenation catalyst is too high, the aldehyde may be formed in the distillation/purification step.

Then, in the invention, the crude alcohol obtained by hydrogenation is purified (hereinafter, sometimes referred to as purification system or purification step).

In the invention, the purification of the crude alcohol is usually achieved by means of a distillation column. As by-products to be separated, there are high-boiling components such as esters, acetals, and ethers formed by esterification, acetalization, etherification, and the like that are side reactions at the hydrogenation reaction, and low-boiling components such as decomposed products thereof, unreacted aldehyde, and isomer alcohols. However, among the ethers, some may behave as low-boiling components with forming azeotropes with alcohols.

In the invention, the distillation is not particularly limited but is usually carried out under atmospheric pressure or reduced pressure, preferably under reduced pressure. The preference is for the purpose of decreasing heat load at the bottom of the distillation column and also lowering the temperature level of the reboiler heat source.

Specifically, it is preferred to run the distillation under the condition of a bottom temperature of 150° C. or lower.

In the invention, the distillation column is not limited and use can be made of a distillation column optionally having a reflux drum, a condenser, a reboiler, and/or a preheater. Of course, the distillation column may have the other ancillary equipments according to need. Moreover, the plate number of the distillation column may be suitably determined.

In the invention, since dissolved gases such as hydrogen, methane, and nitrogen are dissolved in the crude alcohol, it is preferred to separate them prior to the distillation. After the separation of the dissolved gases, the product alcohol is taken out by means of the distillation column. In this connection, in addition to the distillation for taking out the alcohol as a final product, the distillation for removing the low-boiling components, the distillation for removing the high-boiling components, and the like distillation may be conducted in combination. Particularly preferably, the distillation for removing the low-boiling components is conducted prior to the distillation for obtaining the alcohol as a final product and the distillation for removing the high-boiling components is conducted after the distillation for obtaining the alcohol.

The following will explain a specific example of the process for producing an alcohol of the invention with reference to FIG. 1.

Hydrogen gas and an aldehyde are fed from the lines 7 and 8 to a hydrogenation reactor 1 packed with a hydrogenation catalyst to carrying out a hydrogenation reaction. The formed liquid is transferred into a gas-liquid separator 2 though a line 9 and dissolved gases are separated in the gas-liquid separator 2. The dissolved gases are discharged into the outside of the system through a line 11.

After the separation of the dissolved gases, the formed liquid is transferred through a line 10 into a catalyst powder-removing apparatus 3, where the catalyst powder is removed. Thereafter, the liquid is fed to a low-boiling component-separating distillation column 4, where low-boiling components are separated. Passing through a line 13, the separated low-boiling components are typically stored in a tank or the like as a fuel oil and burned, but it is also possible to recover effective components by further distillation.

The bottom product after the separation of the low-boiling components is fed to a product-purifying distillation column 5 through a line 12 and, after the separation of high-boiling components, a product alcohol is obtained from the top of the distillation column. In this connection, the high-boiling components are transferred into a high-boiling components-separating distillation column 6 together with a product alcohol not separated at the product-purifying distillation column 5 through a line 14 and the high-boiling components are taken out from the bottom of the distillation column through a line 16, while the alcohol is taken out of a line 17.

As above, in the invention, by providing the catalyst-removing step between the hydrogenation step and the distillation/purification step, a highly pure alcohol having a concentration of the aldehyde contained in the product alcohol of 500 wt ppm or less, preferably 100 wt ppm or less, more preferably 50 wt ppm or less can be stably obtained in the process wherein the aldehyde conversion rate in the hydrogenation reaction is 98% or more.

EXAMPLES

The following will explain specific embodiments of the invention in further detail with reference to Examples but the invention is not limited by the following Examples unless it exceeds the gist.

Example 1

Crude nonyl alcohol containing a catalyst powder, which had been obtained by hydrogenating nonyl aldehyde using a solid catalyst, was taken out of a nonyl alcohol plant and the catalyst powder was removed by means of a filter having a mesh size of 0.1 μm (the catalyst concentration after the removal was 10 wt ppm). Then, under a nitrogen atmosphere, 200 mL of the crude nonyl alcohol was charged into a 1 L round-bottom flask and a heating test for 7 hours was carried out under a pressure of 60 mmHgA at a temperature of 136° C.

The results are shown in Table 1.

Comparative Example 1

A heating test for 7 hours was carried out in the same manner as in Example 1 except that a powder of a solid hydrogenation catalyst (nickel and chromium as active components had been supported on diatomaceous earth) was added to crude nonyl alcohol taken out of the same nonyl alcohol plant as in Example 1 so that the catalyst concentration became 1160 ppm.

The results are shown in Table 1.

Comparative Example 2

This example was carried out in the same manner as in Comparative Example 1 except that the heating time was changed to 14 hours.

The results are shown in Table 1.

TABLE 1

|  | Crude nonyl alcohol solution | Example 1 | Comparative Example 1 | Comparative Example 2 |
|---|---|---|---|---|
| Content of hydrogenation catalyst | — | — | 1160 ppm | 1160 ppm |

TABLE 1-continued

|  | Crude nonyl alcohol solution | Example 1 | Comparative Example 1 | Comparative Example 2 |
|---|---|---|---|---|
| Pressure | — | 60 mmHgA | 60 mmHgA | 60 mmHgA |
| Atmosphere | — | Nitrogen | Nitrogen | Nitrogen |
| Temperature | — | 136° C. | 136° C. | 136° C. |
| Heating time | — | 7 hours | 7 hours | 14 hours |
| Isononyl aldehyde | 0.0111 wt % | 0.0144 wt % | 0.1826 wt % | 0.322 wt % |
| High-boiling component 1 | 0.709 wt % | 0.533 wt % | 0.596 wt % | 0.706 wt % |
| High-boiling component 2 | 0.452 wt % | 0.227 wt % | 0.249 wt % | 0.109 wt % |
| High-boiling component 3 | 0.171 wt % | 0.216 wt % | 0.243 wt % | 0.109 wt % |
| High-boiling component 4 | 0.011 wt % | 0.000 wt % | 0.000 wt % | 0.000 wt % |
| High-boiling component in total | 1.343 wt % | 0.976 wt % | 1.087 wt % | 1.005 wt % |

In the Table 1, the high-boiling components 1 to 4 mean the following substances.
The high-boiling component 1: C18 ether
The high-boiling component 2: C8 aldol
The high-boiling component 3: C20 acetal
The high-boiling component 4: trimer of C9 aldehyde From the above Example 1 and Comparative Examples 1 and 2, it is revealed that the formation of aldehyde can be remarkably suppressed by removing the powder of the hydrogenation catalyst.

Example 2

Under an air atmosphere, 100 cc of a 2-ethylhexanol sample was charged into a 200 cc round-bottom flask and a powder obtained by supporting nickel and chromium as active components on diatomaceous earth was added thereto as a hydrogenation catalyst so that catalyst concentration became 14 wt ppm. The temperature was elevated over the period of about 5 minutes and sampling was performed after 0 minute, 10 minutes, and 60 minutes from the point of time when the temperature reached 140° C., whereby the concentration of 2-ethylhexanal as an aldehyde was analyzed.

The results are shown in Table 2.

Comparative Example 3

This example was carried out in the same manner as in Example 2 except that the hydrogenation catalyst was added so as to be 0.3 wt %.

The results are shown in Table 2.

TABLE 2

|  | Example 2 | Comparative Example 3 |
|---|---|---|
| Content of hydrogenation catalyst | 14 wt ppm | 0.3 wt % |
| Temperature | 140° C. | 140° C. |
| 2-Ethylhexanal |  |  |
| after 0 minute | 0 wt % | 0.0047 wt % |
| after 10 minutes | 0.0072 wt % | 0.4327 wt % |
| after 60 minutes | 0.0420 wt % | 0.5680 wt % |

From the above Example 2 and Comparative Example 3, it is revealed that the formation of aldehyde can be remarkably suppressed by removing the powder of the hydrogenation catalyst even under an air atmosphere.

While the invention has been described in detail and with reference to specific embodiments thereof, it will be apparent to one skilled in the art that various changes and modifications can be made therein without departing from the spirit and scope thereof.

This application is based on a Japanese patent application filed on Dec. 4, 2002 (Application No. 2002-352760), the entire contents thereof being hereby incorporated by reference.

INDUSTRIAL APPLICABILITY

According to the present invention, the aldehyde formation in a purification system can be remarkably reduced and a product alcohol having a high quality can be stably produced at any time.

The invention claimed is:

1. A process for producing a purified alcohol, the process comprising
    hydrogenating an aldehyde in a reactor packed with a hydrogenation catalyst to form a crude alcohol, and
    purifying the crude alcohol by distillation to produce the purified alcohol;
    wherein the hydrogenation reaction is carried out in the liquid phase,
    wherein, during the hydrogenation process, some of the packed hydrogenation catalyst escapes into the reaction solution in the form of a powder,
    wherein most of the powdered hydrogenation catalyst is removed from the reaction solution via filtration after the hydrogenation of the aldehyde and before distillation of the crude alcohol
    wherein the crude alcohol is subjected to distillation/purification in the presence of the remaining powdered hydrogenation catalyst
    such that a dehydrogenation reaction of the alcohol to the aldehyde is suppressed,
    wherein the aldehyde contained in the purified alcohol, after distillation/purification, is 0.05 wt% or less, and
    wherein the amount of the powdered catalyst present during the distillation/purification of the crude alcohol is present in a positive amount of 100 ppm or less.

2. The process of claim 1, wherein a conversion rate of the aldehyde is 98% or more in the hydrogenation step.

3. The process of claim 1, wherein a conversion rate of the aldehyde to the crude alcohol is 99.99%.

4. The process of claim 1, wherein the aldehyde comprises 3 to 10 carbon atoms.

5. The process of claim 4, wherein the aldehyde is formed by hydroformylation of an olefin.

6. The process of claim 1, wherein the hydrogenation is carried out at a temperature of from 40 to 200° C.

7. The process of claim 1, wherein the pressure during the hydrogenation reaction ranges from 1 to 150 atm.

8. The process of claim 1, wherein the purified alcohol has an aldehyde concentration of 50 wt ppm or less.

9. The process of claim 1, wherein the catalyst comprises an active component, and wherein the active component comprises at least metal selected from the group consisting of nickel, chromium, and copper.

10. The process of claim 9, wherein the active component of the catalyst is supported on diatomaceous earth.

11. The process of claim 9, wherein the active component of the catalyst is supported on celite.

12. The process of claim 1, wherein the aldehyde is butyraldehyde.

13. The process of claim 1, wherein the aldehyde is heptyl aldehyde.

14. The process of claim 1, wherein the aldehyde is nonylaldehyde.

15. The process of claim 1, wherein the aldehyde is propionaldehyde.

16. The process of claim 1, wherein the aldehyde is undecyl aldehyde.

17. The process of claim 1, wherein the aldehyde is tridecyl aldehyde.

18. The process of claim 1, wherein the aldehyde is hexadecyl aldehyde.

19. The process of claim 1, wherein the aldehyde is 2-ethylhexenal.

* * * * *